United States Patent [19]

Mitchell

[11] 4,454,987

[45] Jun. 19, 1984

[54] DISPENSING FRAGRANCES

[75] Inventor: Peter W. D. Mitchell, Freehold, N.J.

[73] Assignee: Union Camp Corporation, Wayne, N.J.

[21] Appl. No.: 403,157

[22] Filed: Jul. 29, 1982

[51] Int. Cl.³ .............................................. A61L 9/04
[52] U.S. Cl. ......................................... 239/6; 239/44; 239/53
[58] Field of Search .......................... 239/6, 34, 44–47, 239/49–51.5, 53–59; 568/840, 875; 260/448 R, 448 A; 422/28, 29, 36; 252/522 A

[56] References Cited

U.S. PATENT DOCUMENTS 2,961,452 11/1960 Raphael .......................... 568/875 X
3,475,476 10/1969 Cragg et al. .................... 568/840 X
3,567,118 3/1971 Shepherd et al. ................ 239/34 X Primary Examiner—Andres Kashnikow
Attorney, Agent, or Firm—Kane, Dalsimer, Kane, Sullivan and Kurucz

[57] ABSTRACT

Disclosed is a method and apparatus for dispensing fragrances of odorant, alcohols over prolonged periods of time.

11 Claims, 2 Drawing Figures

DISPENSING FRAGRANCES

BACKGROUND OF THE INVENTION

1. Field of the Invention

The invention relates to methods and devices of dispensing fragrances and more particularly relates to a method and means of dispensing the fragrance of an odorant alcohol over a prolonged period of time.

2. Brief Description of the Prior Art

A number of alcohols have been used as odorants, i.e.; to provide a masking odor in soaps, cosmetics, room air fresheners and the like. Illustrative of such alcohols are terpene alcohols such as citronellol (3,7-dimethyl-6-octen-1-ol) which has the peppery sweet fragrance of certain roses and geraniol (3,7-dimethyl-2,6-octadien-1-ol) which has the sweet fragrance of geraniums. Unfortunately, these and like alcohols are relatively volatile under ordinary room temperature conditions and quickly dissipate from carrier compositions into the air where their fragrance is eventually lost by dilution.

By the method of the present invention, the fragrance of an odorant alcohol such as citronellol, geraniol or the like may be dispensed from a carrier over prolonged periods of time. The advantage is economic and an important marketing edge.

SUMMARY OF THE INVENTION

The invention comprises a method of dispensing the fragrance of an odorant alcohol, which comprises;

providing in a moisture-impermeable, moisture-free package, a hydrophilic carrier member impregnated with the hydrolysable aluminate of an odorant alcohol; opening the package; and exposing the carrier member to moisture under conditions promulgative of hydrolysis of the aluminate impregnant;

whereby the odorant alcohol is produced by hydrolysis of the aluminate and released from the carrier member over a period of time.

The invention also comprises the moisture-free package of the invention, described above. The package and the method of the invention are useful to dispense the fragrance of an odorant alcohol over a prolonged period of time.

DETAILED DESCRIPTION OF THE PREFERRED EMBODIMENTS OF THE INVENTION

Odorant alcohols and methods of their preparation are well known. Representative of volatile alcohols useful as odorants, i.e.; to provide pleasant, masking odors are citronellol, geraniol, linalool, 1-octanol, menthol, phenylethanol, benzyl alcohol, leaf alcohol (cis-3-hexenol) and the like.

The odorant alcohols are readily obtained by hydrolysis of the corresponding aluminates; see for example the U.S. Pat. No. 2,961,452. The aluminates of odorant alcohols are also well known compounds as is the method of their preparation. General methods of their preparation are described, for example, in U.S. Pat. Nos. 2,961,452 and 3,475,476.

According to the method of the present invention, the hydrolysable aluminate of the odorant alcohol is provided, impregnated in a hydrophilic carrier member. Initially, the carrier member is advantageously moisture-free, so that the aluminate is stable in the carrier. The impregnated carrier is advantageously packaged in a moisture-proof material, to maintain stability and shelf-life of the dispenser until it is ready for use.

A wide variety of moisture-free, hydrophylic carrier members may be employed in the method and article of the invention. Representative of such carrier members are non-aqueous soap compositions, water-permeable, synthetic polymeric resin compositions such as hydrophilic polyurethane foam compositions, paper, textile wick materials and the like. The selection of a particular carrier member will depend on the area or article to be odorized, as will be appreciated by those skilled in the art.

The term "hydrophilic carrier member" as used herein means that the carrier member, upon contact with water vapor or water, will absorb the same.

Figure 1:
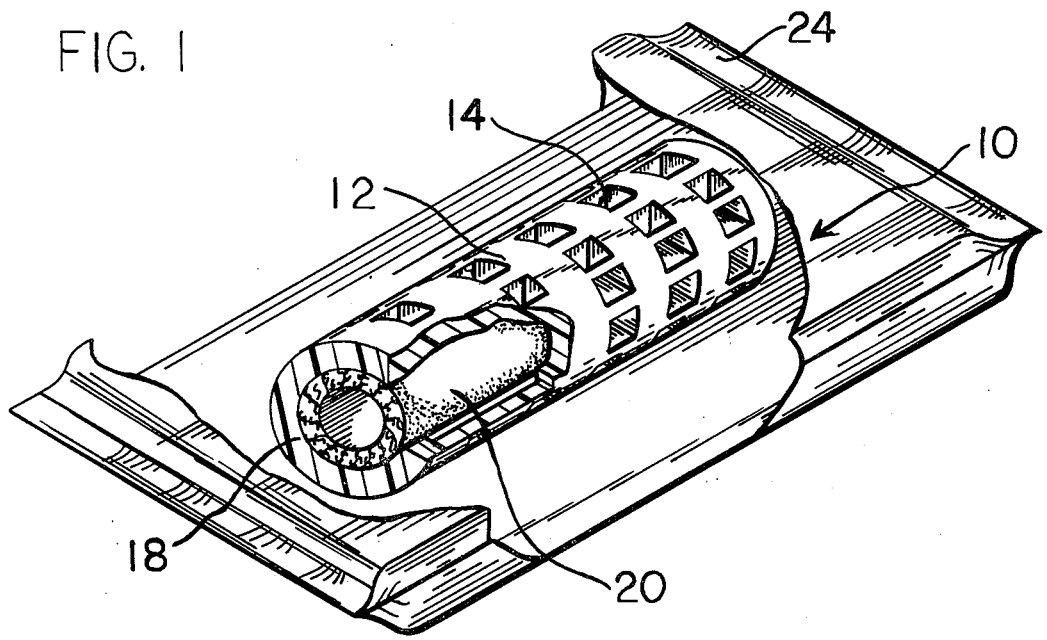
FIG. 1 is a view-in-perspective of an embodiment dispenser device of the invention.
Figure 2:
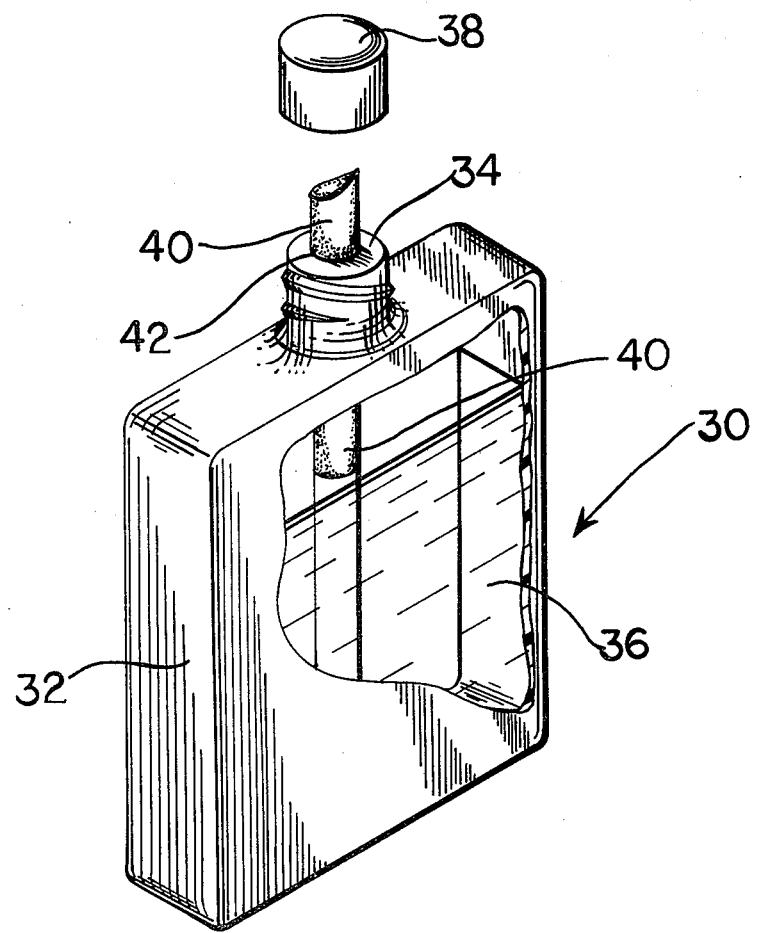
FIG. 2 is a view-in-perspective of another embodiment dispenser device of the invention.

Those skilled in the art will gain a greater appreciation of the invention from the following description of certain preferred embodiments of the invention, when read in conjunction with the drawings of FIGS. 1 and 2.

FIG. 1 is a view-in-perspective of an embodiment dispenser 10 device of the invention. The dispenser device 10 comprises a hollow tube 12, preferably fabricated from a synthetic, polymeric resin such as polyethylene, polycarbonate and like polymeric resins. The tube 12 bears a plurality of apertures 14 in the sidewall thereof, permitting free communication between the interior of the tube 12 and the exterior of the tube 12. The tube 12 has an open end 18 so that air can freely pass into the tube 12 and through the apertures 14 via end 18, or the air flow may be reversed, i.e.; with access through the aperture 14, exiting through end 18. In the FIG. 1, tube 12 has been partially cut away to show an insert 20 of a porous, air-permeable, carrier member 20 lining the inside of the tube 12. The carrier member 20 does not substantially impede air flow through the tube 12 as described above. The carrier member 20 is impregnated with the aluminate of a alcohol known to be an odorant.

As also shown in FIG. 1, the fragrance dispenser 10 is sealed within a moisture-proof foil 24 (partially peeled back to show the contained dispenser 10). The moisture-proof packaging permits one to isolate the dispenser 10 under moisture-free conditions so that the aluminate impregnated in the carrier member 20 is maintained in a stable state, free of hydrolytic activity. The fragrance dispenser 10 may be employed as a room air freshener by unsealing the foil 24 and placing the dispenser 10 in a locality where air, containing normal amounts of humidity, has free access to passage through the tube 12, member 20 and apertures 14. As moisture laden air passes through the dispenser 10, the moisture absorbing carrier member 20 captures and retains some of the moisture. When sufficient moisture is available, under ordinary room temperature conditions, it acts to hydrolyze the aluminate impregnate, whereby the odorant alcohol is generated, volatilized in the passing air and carried into the room air. The release of alcohol fragrance as an odorant, is a room air freshener.

FIG. 2 is a view-in-perspective of another embodiment dispenser 30 device of the invention. Dispenser 30 comprises a glass or ceramic container 32 having a sealed opening 34 and containing a liquid aluminate 36 of an odorant alcohol. A moisture-proof cap 38 normally closes an aperture 42 in the closed end 34. In use, the cap 38 is removed to reveal a capillary wick 40 passing through and in close relationship with the aperture 42. The exposed portion of the capillary wick 40 carries the aluminate 36 out of the container 32 so that it is exposed upon removal of cap 38 to moisture laden air. The wick 40, absorbs some of the air moisture, thereby providing water for hydrolysis of the aluminate 36 in the exposed portion of the capillary wick 40. Again, as in the dispenser 10, the odorant alcohol is generated and released by evaporation into the air to provide a room air freshener. As the alcohol is produced, by-product aluminum hydroxide residues may form on the wick surfaces. Periodic scraping of the wick will remove these residues if they tend to block wick interstices.

Those skilled in the art will appreciate that any variations of the above described preferred embodiments 10 and 30 may be made without departing from the spirit and scope of the invention. For example, the aluminate compositions may be included in soaps, cosmetics, antiperspirants and like materials as carriers. These carriers may then be sealed within moisture-proof packages until their use is required. Upon unsealing them and exposing them to moisture in the form of water vapor or through contact with water (in showers, etc.) there is a slow release of the fragrance of the odorant alcohol generated by hydrolysis of the aluminate.

A further advantage of the use of aluminates in deodrant or anti-perspirant compositions is that the aluminum hydroxide, formed during slow release of the alcohol odorant, is itself a commonly used ingredient of such formulations.

The following examples show and describe the manner and process of carrying out the invention and set forth the best mode contemplated by the inventor but are not to be considered as limiting the spirit and scope of the invention.

EXAMPLE 1

A set of fragrance testing papers were dipped to a depth of one-half inch in citronellol. Another set was similarly dipped, in a solution of tricitronelloxyaluminum. Both sets of papers were kept in the open at room temperature (circa 26° C.) and ambient humidity. Both sets of papers were evaluated for odor daily. After 2 days, the citronellol saturated papers were found to be odorless. After 5 days, the tricitronelloxyaluminum saturated papers were still distinguishable by their citronellol odor.

EXAMPLE 2

The procedure of Example 1, supra., was repeated except that in place of the citronellol and the tricitronelloxyaluminum as used therein, various odorant alcohols and their aluminates were used. The aluminates were made by heating the alcohol (6 g) with aluminum isopropylate (4 g) at 80° C. under vacuum (20 mm) for 5 hours. After 65 hours, the strengths of the odor above the saturated papers were those given in the Table below.

TABLE

| ALCOHOL | ODOR RELEASE (FROM ALCOHOL) | ODOR RELEASE (FROM ALUMINATE) |
|---|---|---|
| 1. Geraniol | Odorless | Strong |
| 2. Menthol | Odorless | Strong |
| 3. trans-Piperitol | Odorless | Strong |
| 4. 2-Phenethyl | Slight odor of phenyl acetic acid | Strong |
| 5. n-Octanol | Odorless | Strong |
| 6. Linalool | Odorless | Moderate |
| 7. α-terpineol | Odorless | Slight |

What is claimed:
1. A method of dispensing the fragrance of an odorant alcohol, which comprises;
   providing in a moisture impermeable, moisture-free package, a hydrophilic carrier member impregnated with the hydrolyzable aluminate of an odorant alcohol;
   opening the package; and
   exposing the carrier member to moisture under conditions promulgative of hydrolysis of the aluminate impregnant;
   whereby the odorant alcohol is produced by hydrolysis of the aluminate and released from the carrier member over a period of time.
2. The method of claim 1 wherein the aluminate is tricitronellyloxyaluminate.
3. The method of claim 1 wherein the alcohol is geraniol.
4. The method of claim 1 wherein the alcohol is menthol.
5. The method of claim 1 wherein the alcohol is transpiperitol.
6. The method of claim 1 wherein the alcohol is 2-phenethyl.
7. The method of claim 1 wherein the alcohol is n-octanol.
8. The method of claim 1 wherein the alcohol is linalool.
9. The method of claim 1 wherein the alcohol is α-terpineol.
10. A dispenser for dispensing the fragrance of an odorant terpene alcohol, which comprises:
    a hydrophilic carrier member impregnated with the hydrolyzable aluminate of an odorant terpene alcohol, packaged under moisture-free conditions in a moisture-impermeable package means.
11. The dispenser of claim 10 wherein said aluminate is tricitronelloxyaluminum.

* * * * *